United States Patent
Piantoni et al.

(10) Patent No.: US 10,603,222 B2
(45) Date of Patent: Mar. 31, 2020

(54) FORMING POCKET AND METHOD FOR MAKING A FORMING POCKET

(71) Applicant: GDM S.p.A., Bologna (IT)

(72) Inventors: Matteo Piantoni, Albino (IT); Valerio Soli, Bologna (IT)

(73) Assignee: GDM S.p.A., Bologna (IT)

( * ) Notice: Subject to any disclaimer, the term of this patent is extended or adjusted under 35 U.S.C. 154(b) by 129 days.

(21) Appl. No.: 15/523,815

(22) PCT Filed: Nov. 3, 2015

(86) PCT No.: PCT/IB2015/058487
§ 371 (c)(1),
(2) Date: May 2, 2017

(87) PCT Pub. No.: WO2016/071833
PCT Pub. Date: May 12, 2016

(65) Prior Publication Data
US 2017/0312139 A1 Nov. 2, 2017

(30) Foreign Application Priority Data
Nov. 5, 2014 (IT) .............................. BO2014A0613

(51) Int. Cl.
*A61F 13/15* (2006.01)
*A61F 13/00* (2006.01)

(52) U.S. Cl.
CPC .. *A61F 13/15626* (2013.01); *A61F 13/15658* (2013.01); *A61F 13/15764* (2013.01)

(58) Field of Classification Search
CPC .......... A61F 13/15626; A61F 13/15658; A61F 13/15764
See application file for complete search history.

(56) References Cited

U.S. PATENT DOCUMENTS 2,306,201 A * 12/1942 Wiles ..................... C10G 73/00
  208/20
3,913,210 A * 10/1975 Broad .................... B21D 47/00
  228/181

(Continued)

FOREIGN PATENT DOCUMENTS

| CN | 101534770 A | 9/2009 |
| JP | 2010509519 A | 3/2010 |
| WO | 2008061178 A2 | 5/2008 |

OTHER PUBLICATIONS

International Search Report and Written Opinion Application No. PCT/IB2015/058487 Completed Date: Feb. 1, 2016; dated Feb. 15, 2016 9 Pages.

(Continued)

*Primary Examiner* — Jacob T Minskey
(74) *Attorney, Agent, or Firm* — Whitmyer IP Group LLC

(57) ABSTRACT

A forming pocket suitable for forming conglomerates from particulate material to be used as an absorbent padding for hygienic products, includes an external forming substrate for receiving particulate material, the substrate having openings and a shape conjugated to a form of the absorbent padding to be made. The forming pocket includes a grid supporting structure, which has openings and is coupleable with the substrate to support the substrate during suction of particulate material through the substrate. The supporting structure has an external surface configured to contact the substrate and has a shape conjugated to the shape of the substrate. A method of making the forming pocket includes obtaining from at least one first metal sheet first and second sets of elements having a plurality of cuts, and wedging the elements of the first set with the elements of the second set via the cuts to make the grid supporting structure.

8 Claims, 8 Drawing Sheets

(56) References Cited

U.S. PATENT DOCUMENTS

| | | | | |
|---|---|---|---|---|
| 4,370,515 | A * | 1/1983 | Donaldson | H05K 9/0032 174/387 |
| 4,666,647 | A * | 5/1987 | Enloe | A61F 13/15658 19/148 |
| 4,761,258 | A * | 8/1988 | Enloe | A61F 13/15658 264/118 |
| 6,098,249 | A * | 8/2000 | Toney | A61F 13/15577 19/296 |
| 6,330,735 | B1 * | 12/2001 | Hahn | A61F 13/15626 19/296 |
| 7,824,775 | B2 * | 11/2010 | Copley | B23K 15/0006 428/593 |
| 2001/0043834 | A1 | 11/2001 | Mullen | |
| 2008/0113052 | A1 | 5/2008 | Van Valkenburgh et al. | |
| 2008/0113054 | A1 * | 5/2008 | Fegelman | A61F 13/15626 425/81.1 |

OTHER PUBLICATIONS

Japanese Office Action and Translation Application No. 2017-523232 dated Jun. 28, 2019 9 pages.
Chinese Office Action and Translation Application No. 201580059566.4 dated Dec. 13, 2019 13 pages.

* cited by examiner

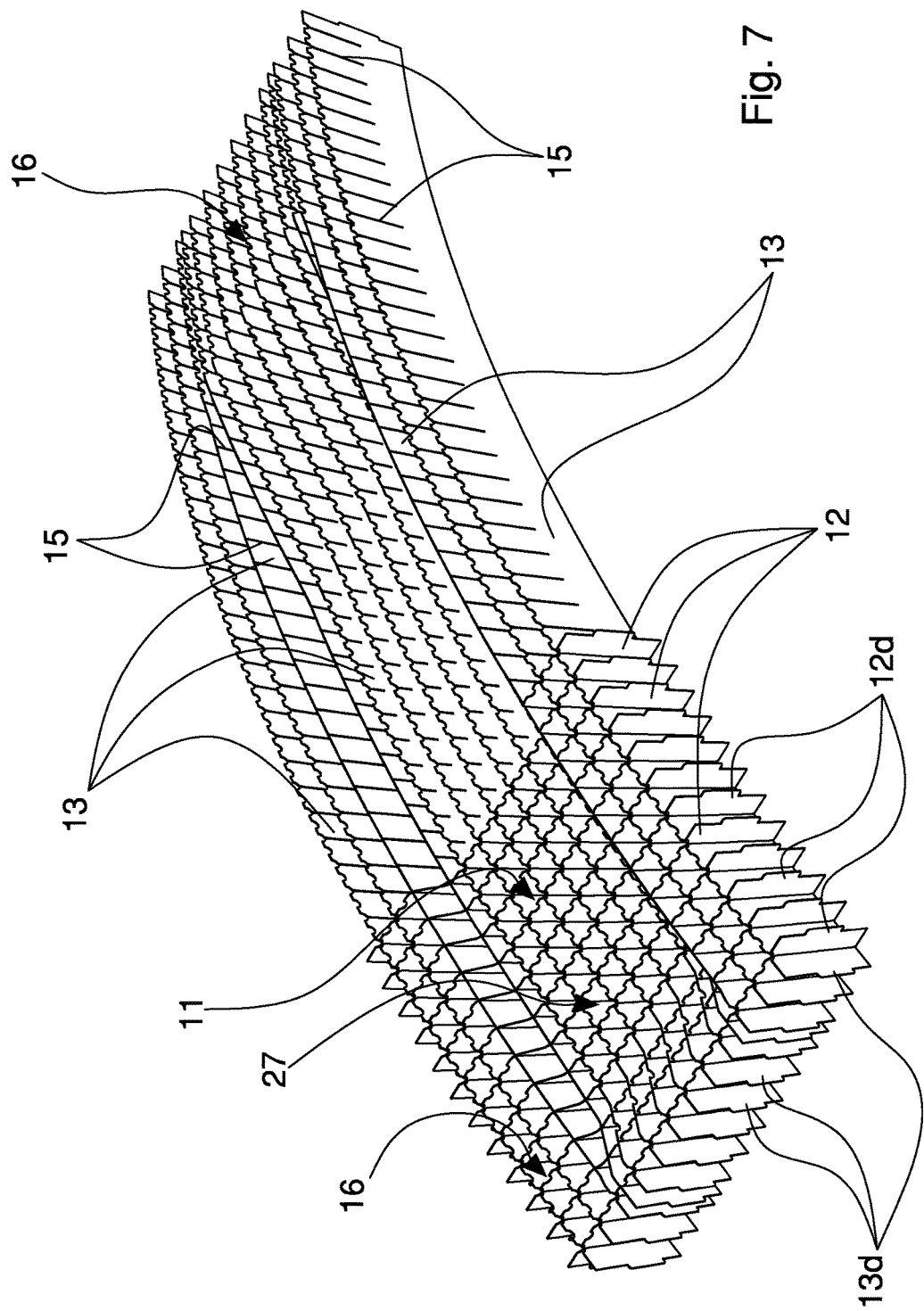

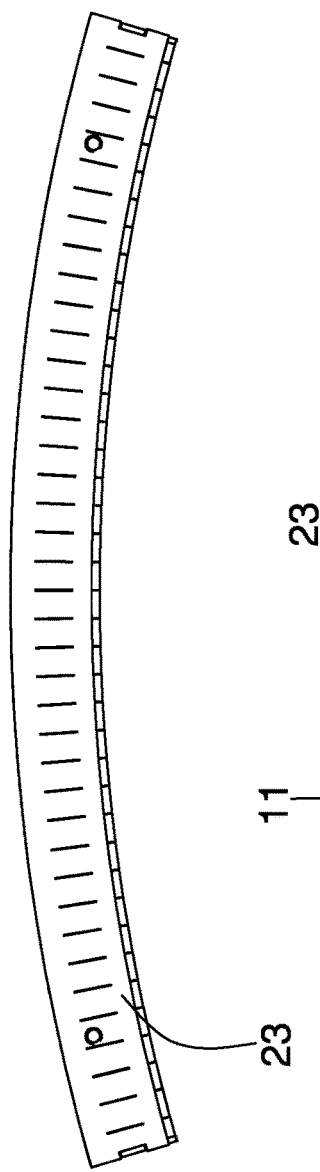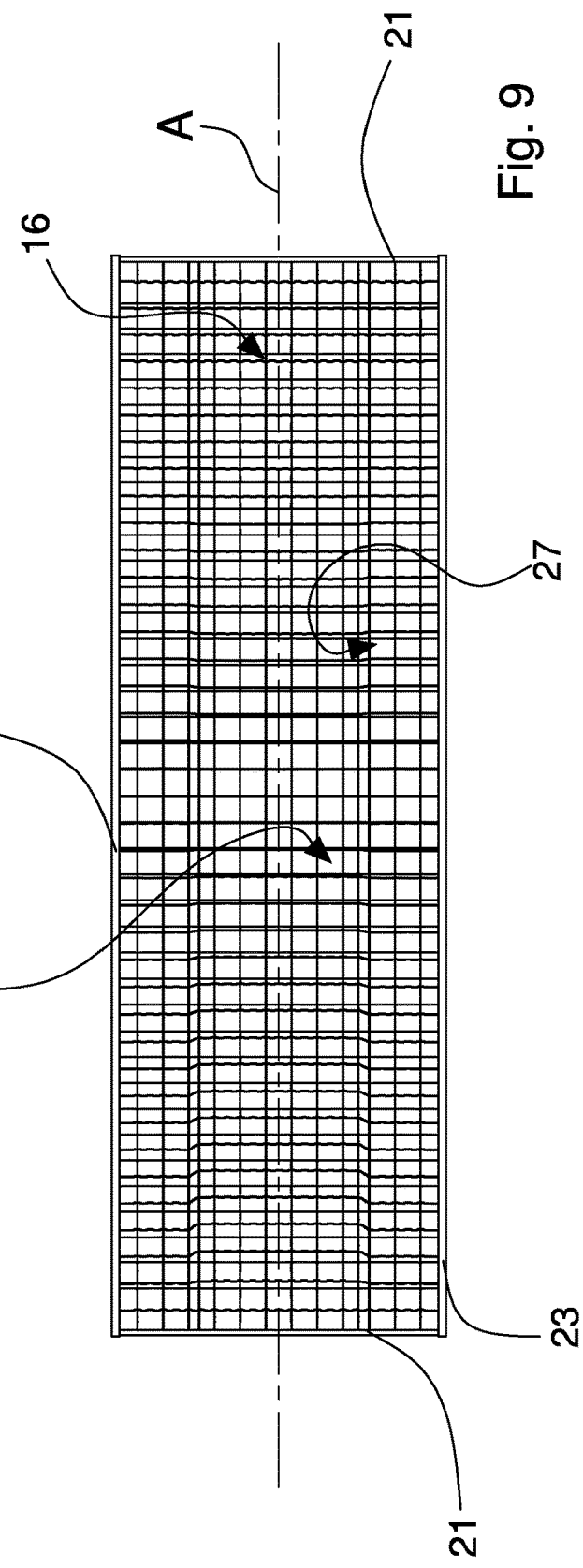

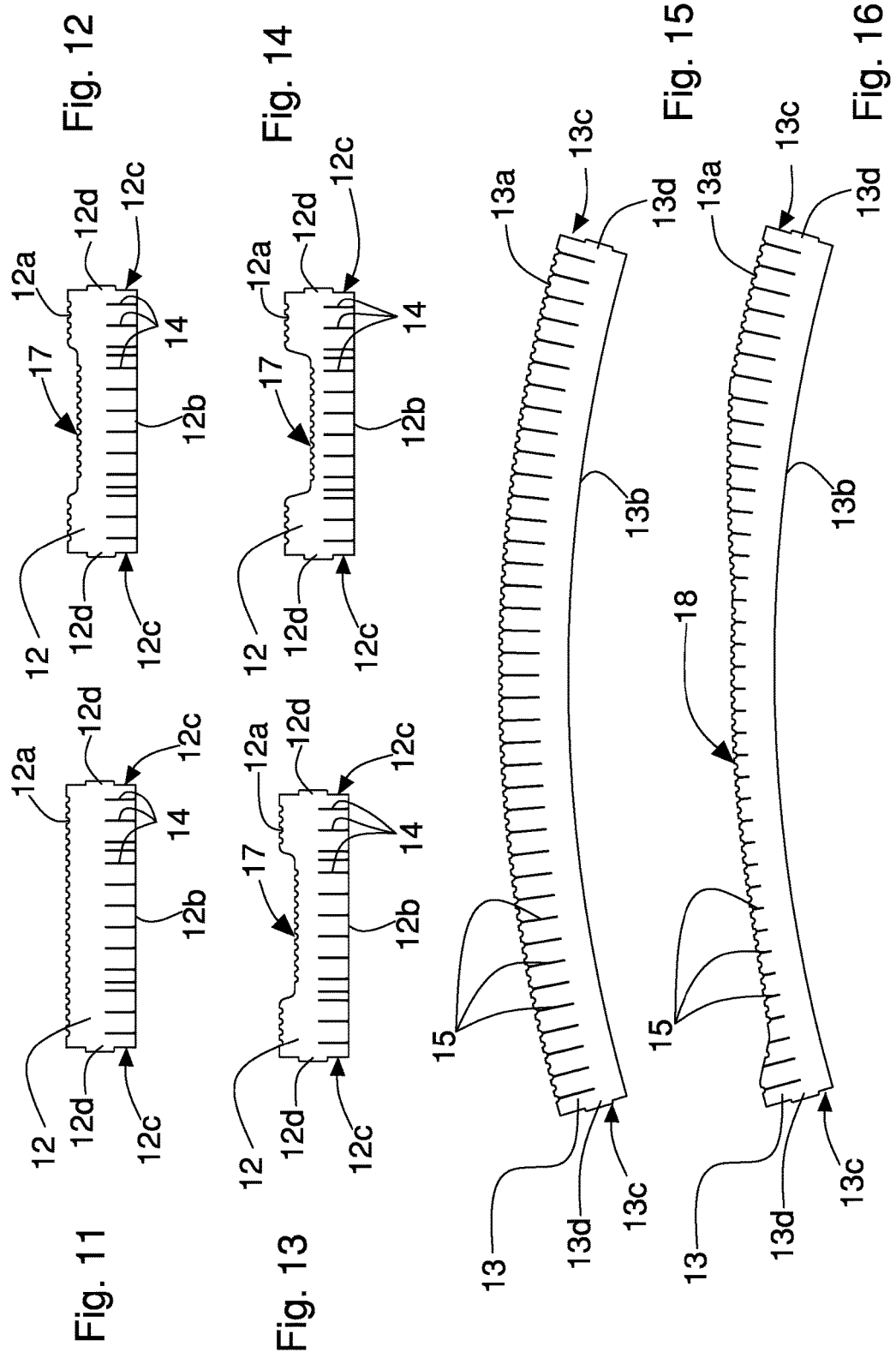

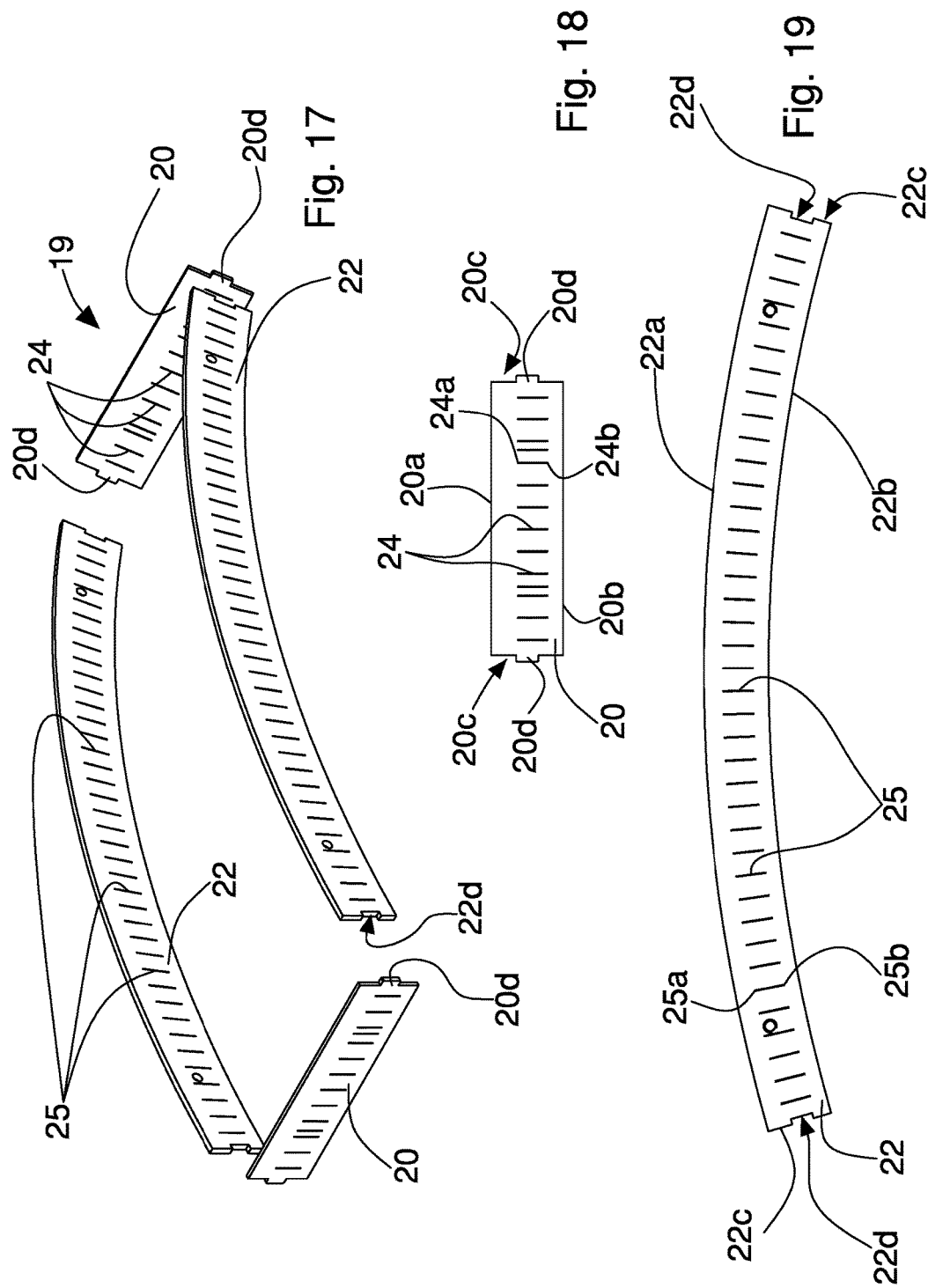

FORMING POCKET AND METHOD FOR MAKING A FORMING POCKET

TECHNICAL FIELD

The present invention relates to a forming pocket for forming absorbent padding for hygienic products, the forming pocket comprising an external forming substrate, suitable for receiving particulate material and forming conglomerates from the particulate material, and a grid supporting structure that is coupleable with the external forming substrate. The present invention further relates to a method for making the grid supporting structure of the forming pocket. The present invention is advantageously used in a forming conveyor of hygienic products comprising a plurality of forming pockets that are suitable for forming respective absorbent conglomerates for hygienic products in an apparatus for forming hygienic products, to which reference will be made below without loss of generality.

BACKGROUND

As known, hygienic products, in particular diapers for babies, sanitary towels or products for adult incontinence, comprise a layer of absorbent padding that is enclosed between a layer of nonwoven fibre and an impermeable layer, for example polyethylene. The absorbent padding is made of a conglomerate of cellulose fibres and/or of particles of superabsorbent material which is formed in an apparatus for forming such hygienic products.

In order to make anatomically shaped hygienic products, shaping the absorbent padding is known, according to the desired anatomical shape before enclosing the absorbent padding between the layer of nonwoven fibre and the impermeable layer.

The forming apparatus (which is not illustrated) comprises a forming drum 1 (illustrated schematically in FIGS. 1 to 3) of absorbent padding, the outer periphery of which is provided with a plurality of sucking forming pockets, and is supplied, at the periphery thereof, with a flow of particulate material. In each pocket, the fibres of the particulate material are conveyed by a flow of sucking air and are compacted by suction, thus obtaining the absorbent conglomerate, which is also known as fluff, of the required shape.

According to a different embodiment, which is not illustrated, the forming conveyor can comprise a closed loop continuous belt conveyor.

As shown in FIG. 1, the forming drum 1 comprises a plurality of forming pockets 2a shaped, aligned and uniformly distributed along the external surface of the drum 1, and comprising for example a cavity of substantially troncopyramidal shape, for making variable thicknesses of absorbent padding. Alternatively, as shown in FIG. 3, the forming drum 1 can comprise forming pockets 2b shaped, aligned and uniformly distributed along the external surface of the drum 1, and comprising for example an anatomical cavity of rounded shape for making absorbent padding of anatomical shape. Also alternatively, as shown in FIG. 2, the forming drum 1 can comprise a single forming pocket 2c shaped as a single annular cavity for making a web of absorbent padding, to be divided into rectangular portions with subsequent cutting.

Each forming pocket has in other words the desired shape for the padding to be obtained and/or to permit the successive processes for which the absorbent conglomerate is intended. The depth of the forming pocket determines the thickness of the absorbent layer to be made. The forming pockets are typically fixed to spaces of the forming drum of a shape corresponding to the pockets.

The forming pockets have to be perforated to enable the air flow to retain effectively by suction the particles of which the particulate material is made on the surface thereof, but at the same time they have to prevent the powdered material, which is also a component of the particulate material, from traversing the pockets. The openings in the forming pockets thus have to have a reduced dimension and typically it is required for the openings to have a dimension comprised in a range between 0.20 mm and 0.40 mm.

In order to make the forming pockets, which are usually made of metal, it is known to use, for receiving and retaining the particulate material, micro-perforated thin metal plates or micro-perforated metal nets by means of which it is possible to make openings of the desired dimension. Nevertheless, such thin metal plates or such metal nets have a reduced thickness and are thus flexible and easily deformable.

The deformability of the forming pocket during assembling and/or dismantling of the pocket in the forming drum makes handling and cleaning thereof difficult, which cleaning is frequently scheduled at set intervals in order to remove by means of a thorough cleaning any particulate material wedged in the openings of the forming pocket.

In order to ensure the appropriate toughness of the forming pockets, prevent possible deformation thereof and facilitate assembling and dismantling of the forming pockets during maintenance, it is known to support the thin micro-perforated metal plate or the metal net, which makes the forming substrate, by means of a stiff support, which is also perforated to permit the passage of air, supporting the external substrate.

The external substrate has a shape that is conjugated to the form of the absorbent padding to be made whereas the stiff support is of a shape conjugated to the external substrate shape to support appropriately the external substrate and confer toughness thereupon.

As shown by U.S. Pat. No. 4,761,258 and shown in FIGS. 4 and 5 with reference to a forming pocket 2a shaped as in FIG. 1, the external forming substrate 3 is made by a perforated thin metal plate, has a substantially frustoconical cavity 4 and is supported by a supporting structure 5, made as a metal net, which has a corresponding cavity 6, shaped like the cavity 4 and arranged at the cavity 4 of the external forming substrate 3. As an alternative to the metal net 5, the supporting structure can be made by a metal grid 7, shown in FIG. 5 or by means of a honeycomb grid (which is not illustrated), which provides greater toughness than the metal net and are thus usually preferred.

It should be noted that the absorbent padding that is obtainable from the forming pocket of FIG. 4 is a portion with a greater thickness at the frustoconical cavity 4 of the forming pocket 2a. Shaped padding of variable thickness forces the external forming substrate 3 to have at least one concave zone like the cavity 4 and consequently forces also the external surface of the supporting structure 5, intended to contact the external forming substrate 3 to have a respective concave zone, and i.e. the cavity 6. In addition, when the forming pocket is fixed to the forming drum, the inner surface of the supporting structure, opposite the external surface, is also curved because it is intended for contact with the forming drum 1.

The method for making the grid supporting structure thus has a plurality of production steps for making an external surface and/or an inner surface with hollow portions from a flat supporting grid structure, which make the grid supporting structure very expensive.

After obtaining a flat grid by welding together a plurality of drawn metal sheets, the grid is first curved to obtain the inner surface to be rested on the welding drum and is then treated by a process of electroerosion to make the hollow zones of the external surface.

This producing method thus makes it necessary to provide dedicated equipment. Special welding work benches are in fact necessary, on dedicated electroerosion machining work benches, which are very expensive. The electroerosion process is in itself very expensive because it requires dedicated electrodes that are to be regenerated frequently inasmuch as they are subject to wear.

In addition to the dedicated equipment, several machining steps are necessary, which make the production process of each grid supporting structure lengthy and which further require much labour.

It is added that the shape of each grid supporting structure is determined by the shape of the corresponding absorbent padding to be made and that accordingly the equipment dedicated to the production of a specific type of supporting structure has to be modified with the variation of the type of absorbent padding to be made.

SUMMARY

An object of the present invention is to provide a method for making a forming pocket for absorbent padding, which is free of the drawbacks disclosed above and is in particular simple and cheap to make.

One object of the present invention is further to provide a method for making a grid supporting structure in a forming pocket for absorbent padding that enables the shape of the absorbent padding to be made to be varied without needing to replace the production equipment.

An object of the present invention is in addition to provide a method for making a grid supporting structure in a forming pocket for absorbent padding that has great production efficiency in terms of reduced machining time for each supporting structure.

An object of the present invention is further to provide a forming pocket for absorbent padding that comprises a supporting structure that is simple and cheap to make.

According to the present invention, a method is provided for making a forming pocket for absorbent padding according to the attached claims.

According to the present invention, a forming pocket for absorbent padding is further provided according to the attached claims.

BRIEF DESCRIPTION OF THE DRAWINGS

The present invention will now be disclosed with reference to the attached drawings that illustrate some embodiments thereof by way of non-limiting example, in which:

FIG. 7 is a perspective view of the supporting structure of FIG. 6, in an assembling step;

FIG. 8 is a side view of the supporting structure of FIG. 6;

FIG. 9 is a top view of the supporting structure of FIG. 6;

FIGS. 11 to 14 show a frontal view of a plurality of elements of the first set, each shaped in a different manner from one another;

FIGS. 15 and 16 show a frontal view of two elements of the second set, shaped in a different manner;

FIG. 17 shows a perspective view of a stabilising frame of the supporting structure of FIG. 6;

FIG. 18 shows a frontal view of an element of the third set that is suitable for making a front wall of the stabilising frame of FIG. 17; and FIG. 19 shows a frontal view of an element of the fourth set that is suitable for making a side stabilising frame of FIG. 17.

DETAILED DESCRIPTION

In this description, identical elements that are common to the various illustrated embodiments have been indicated by the same numbering.

A forming apparatus (which is not illustrated) for making absorbent padding for hygienic products comprises a forming conveyor of the absorbent padding. A forming drum conveyor has been indicated by 1 in FIGS. 1 to 3 with particular reference to the prior art and for the sake of brevity is not disclosed again below.

The forming conveyor comprises at least one forming pocket (which is not illustrated).

Figure 4:
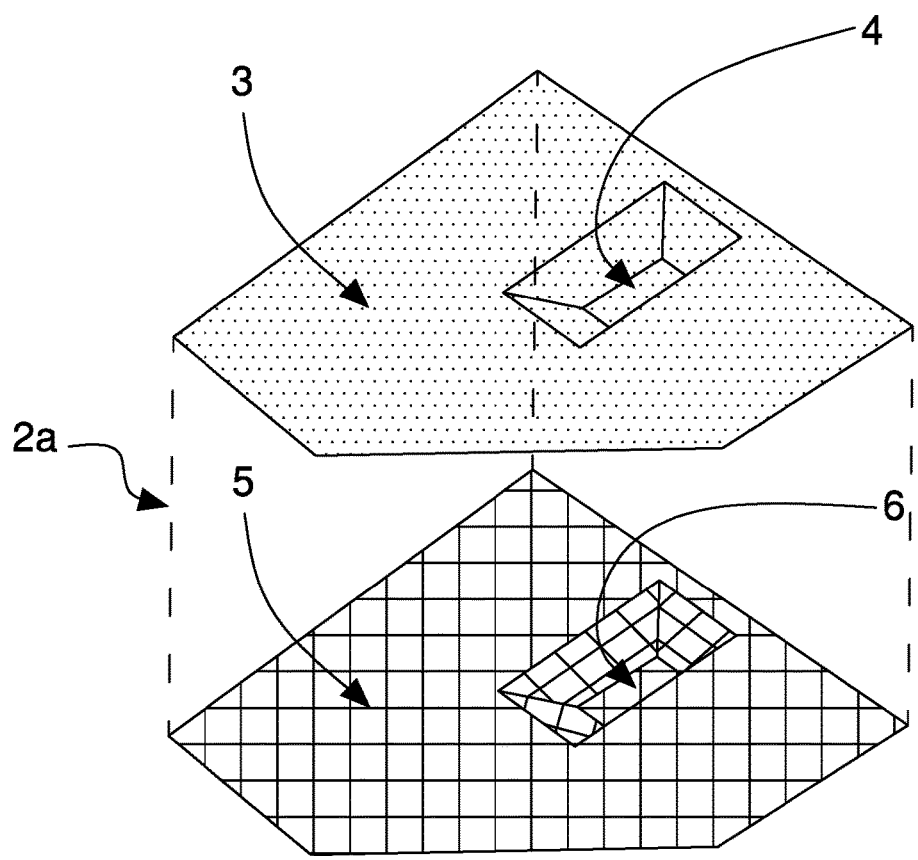
FIG. 4 shows an exploded perspective view of a portion of a forming pocket in which some parts are removed for the sake of clarity, according to the prior art.
Figure 5:
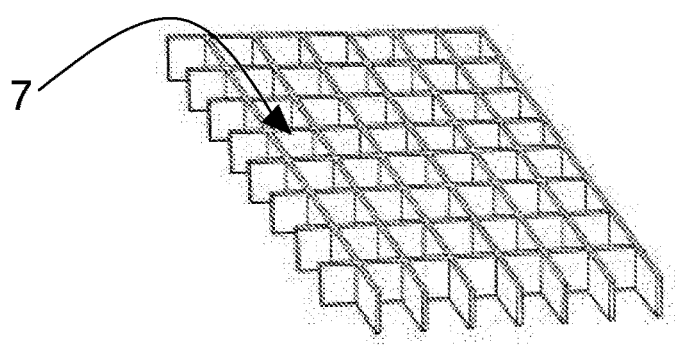
FIG. 5 shows a grid supporting structure, according to the prior art.

The forming pocket is suitable for receiving particulate material and forming conglomerates from the particulate material to be used as absorbent padding for hygienic products. The forming pocket comprises an external forming substrate suitable for receiving the particulate material, which is makeable by means of a metal net or sheet metal, which is provided with openings and has a shape conjugated to the form of the absorbent padding to be made. The external forming substrate, indicated by 3 in FIG. 4, has already been disclosed in detail with particular reference to the prior art and is not disclosed below for the sake of brevity.

Figure 6:
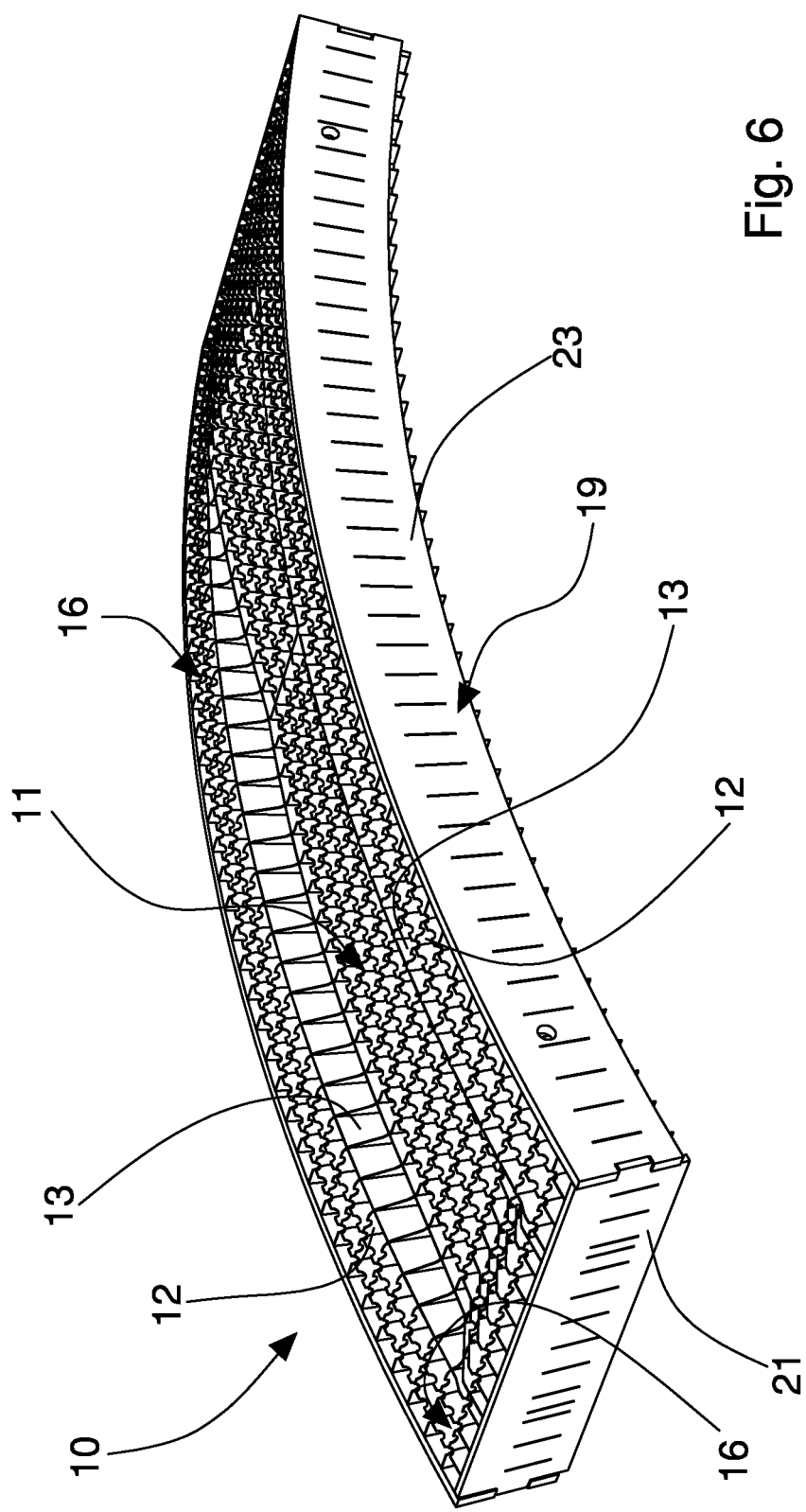
FIG. 6 is a perspective view of the grid supporting structure according to the invention, after assembling has been completed.

In FIG. 6, a grid supporting structure 10 provided with openings is indicated, which is coupled with the external forming substrate to support the external substrate during sucking of the particulate material through the external substrate to form the conglomerate of absorbent material. The external substrate is in particular coupled through superimposing and is fixed to the supporting structure 10.

The supporting structure 10 has an external surface which is intended for contact with the external substrate and is of a shape conjugated to the shape of the external substrate. For example, the supporting structure 10 shown in FIGS. 6 and 7 has an external surface that has a cavity 11, intended for receiving a corresponding cavity (which is not illustrated) of the external substrate. A curved margin surface 16 surrounds the cavity 11 and extends over the remaining part of the external surface of the supporting surface 10.

The supporting structure 10 comprises a first set of elements 12 and a second set of elements 13 made of sheet metal, shown in detail in FIGS. 11 to 16, each of which has a plurality of comb-shaped cuts.

In detail, each element 12 of the first set has a plurality of comb-shaped cuts 14, in particular rectilinear comb-shaped cuts 14, and each element 13 of the second set has a plurality of comb-shaped cuts 15, in particular, which are also rectilinear, by means of which the elements 12 of the first set are suitable for wedging in the elements 13 of the second set to make the grid of the supporting structure 10.

The shape of each element 12 of the first set and the distribution of the respective cuts 14, and further the shape of each element 13 of the second set and the distribution of the respective cuts 15 are selected appropriately because they determine the shape of the grid to be made. Between the elements 12 of the first set and the elements 13 of the second set, sucking cells 27 are defined to enable the particulate material to be sucked, the dimension of which is also selected opportunely as will be seen below in greater detail.

Each element 12 of the first set has an external edge 12a, which is suitable for defining part of the external surface of the supporting structure, an internal edge 12b opposite the external edge 12a and side edges 12c. The external edge 12a, the internal edge 12b and the side edges 12c define the perimeter of each element 12.

Each element 13 of the second set has an external edge 13a, which is also suitable for defining part of the external surface of the supporting structure, an internal edge 13b opposite the external edge 13a and side edges 13c. The external edge 13a, the internal edge 13b and the side edges 13c define the perimeter of each element 13.

It should be noted that the cuts 14 of each element 12 of the first set extend from the internal edge 12b to the external edge 12a without intersecting the external edge 12a and that the cuts 15 of each element 13 of the second set extend from the external edge 13a to the internal edge 13b without intersecting the internal edge 13b.

In this manner, each element 12 of the first set can be wedged above a plurality of elements 13 of the second set, i.e. by pushing, as will be seen below, the internal edge 12b of each element 12 of the first set onto the elements 13 of the second set, in particular from the external edge 13a to the internal edge 13b thereof (FIG. 7).

If the forming pocket and thus also the supporting structure 10 is elongated and it is possible to identify a prevalent extent of the supporting structure along a longitudinal axis A (FIG. 9), the elements 13 of the second set are longitudinal elements whilst the elements 12 of the first set, arranged perpendicularly to the elements 13 of the second set, are transverse elements.

According to a different embodiment of the supporting structure 10 (which is not illustrated), both the elements 12 of the first set and the elements 13 of the second set are transverse to the longitudinal axis A, for example the elements 13 of the second set are tilted by 45° with respect to the longitudinal axis A and the elements 12 of the first set are perpendicular to the elements 13 of the second set.

The internal edge 12b of the elements of the first set 12 is rectilinear and the cuts 14 are substantially perpendicular to the internal edge 12b. The external edge 12a of the elements 12 of the first set on the other hand has a shape that depends on the position of the element in the supporting structure 10, for example along the longitudinal axis A.

For example, the element 12 of the first set shown in FIG. 11 has an external edge 12a that is substantially rectilinear because it is intended to form part of the curved margin surface 16 whereas the external edge 12a of the elements 12 of the first set of FIGS. 12 to 14 has substantially rectilinear side portions that are intended for forming part of the curved margin surface 16 and a hollowed out portion 17 interposed between the rectilinear side portions to define part of the external surface of the cavity 11.

It should be noted that the hollowed out portion 17 of a first element 12 shown in FIG. 12 is shaped differently from the hollowed out portion 17 of a second element 12 shown in FIG. 13 or in FIG. 14, inasmuch as, for example, the external edge 12a of the second element 12 of FIG. 14 is intended to form part of the surface of a bottom of the cavity 11.

As illustrated in FIGS. 15 and 16, the external edge 13a of the elements of the second set 13 is curved and each cut 15 is substantially perpendicular to a tangent of the external edge 13a. The shaped form of the external edge 13a depends on the position of the element 13 in the supporting structure 10, for example according to the distance from the longitudinal axis A.

For example if a first element 13 of the second set shown in FIG. 15 is considered, the external edge 13a is convex and has a curvature radius that is substantially uniform because it is intended to form part of the curved margin surface 16. On the other hand, the external edge 13a of a second element 13 of the second set shown in FIG. 16 has curved side portions intended to form part of the curved margin surface 16 and a hollowed out portion 18 interposed between the curved side portions to define part of the external surface of the cavity 11.

Figure 1:
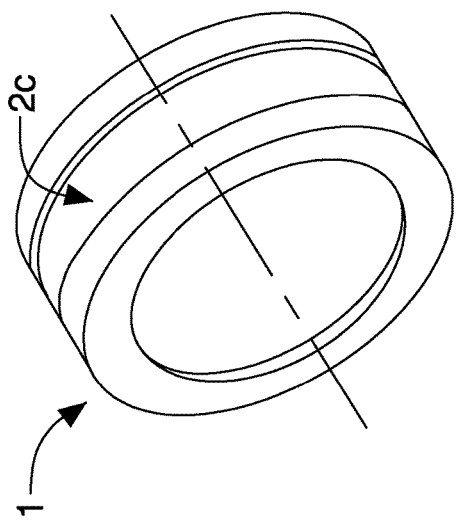
FIGS. 1 to 3 illustrate three perspective schematic views of three alternative embodiments of a forming drum of absorbent padding for hygienic products, according to the prior art.
Figure 3:
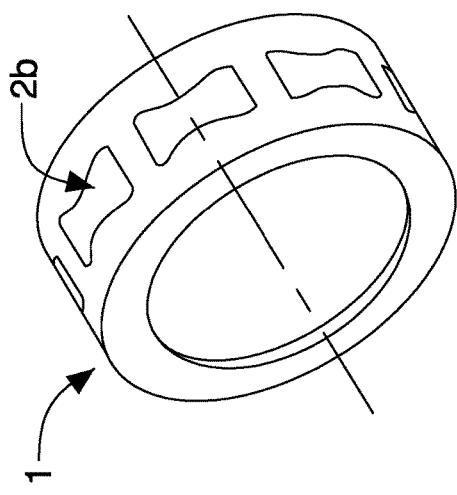
Figure 2:
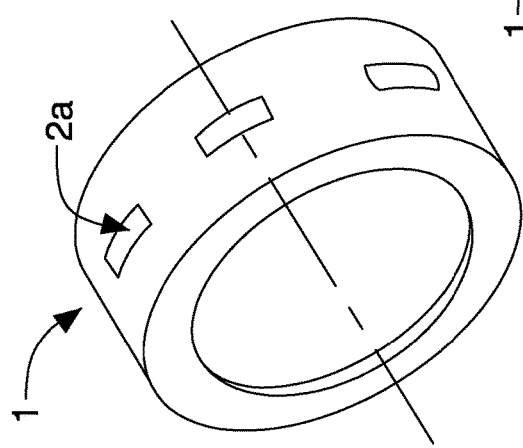

If the forming conveyor is a forming drum, of the type illustrated for example in FIGS. 1 to 3, the supporting structure 10 comprises a curved inner surface, opposite the external surface, intended for contact with the forming drum and of a shape conjugated to an external surface of the forming drum.

The internal edge 13b of each element 13 of the second set is suitable for defining part of said curved inner surface of the supporting structure 10. As is clear from FIGS. 6-8, 15 and 16, the internal edges 13b of the elements 13 of the second set all have the same shape, which corresponds to the shape required for fixing to the forming drum.

It should be noted that the internal edge 12b of the elements of the first set 12 is rectilinear because it is not intended to come into contact with the forming drum but remains suspended between the elements 13 of the second set. According to a different embodiment of the elements 12 of the first set, also the internal edge 12b of the elements 12 of the first set is shaped in the manner intended to define the curved inner surface of the supporting structure 10 intended for fixing to the forming drum.

As shown in FIGS. 6, 8 and 17-19, the supporting structure 10 comprises a stabilising frame 19 comprising a third set of elements 20 made of sheet metal that are suitable for making two frontal walls 21 of the frame 19 that are opposite, a fourth set of elements 22 made of sheet metal that are suitable for making two side walls 23 of the frame 19 that are opposite, in which the third set of elements 20 is suitable for wedging in the fourth set of elements 22 to form the frame.

Each element 20 of the third set and each element 22 of the fourth set have an external edge, identified respectively with 20a and 22a, which is suitable for defining part of the external surface of the supporting structure 10, and an internal edge, identified respectively with 20*b* and 22*b*, opposite the external edge. Each element 20 of the third set and each element 22 of the fourth set have, moreover, side edges 20*c* and 22*c*. The side edges 20*c* of the elements 20 of the third set have protrusions 20*d* of a shape that is complementary to respective recesses 22*d* located in the side edges 22*c* of the elements 22 of the fourth set. The protrusions 20*d* and the recesses 22*d* enable the elements 20 of the third set to wedge in the elements 22 of the fourth set for making the frame 19.

The elements 20 of the third set have a plurality of slots 24, suitable for receiving corresponding protruding ends 13*d* of side edges 13*c* of elements 13 of the second set. The elements 22 of the fourth set have a plurality of slots 25 suitable for receiving corresponding protruding ends 12*d* of side edges 12*c* of elements 12 of the first set.

By wedging the protruding ends 12*d* and 13*d* of the elements 12 of the first set and of the elements 13 of the second set respectively into the slots 25 and 24 of the stabilising frame 19, the grid supporting structure 10 made by wedging together the elements 12 of the first set and the elements 13 of the second set (FIG. 7) is further stabilised by the stabilising frame 19.

It is added that, in order to confer greater toughness on the supporting structure 10 that has been thus made, some points of contact between the elements of the first set 12 and/or the elements 13 and/or the elements of the stabilising frame 19, i.e. the elements 20 of the third set and/or the elements 22 of the fourth set can be welded.

Each slot 24 of each element 20 of the third set extends from a first internal end 24*a* to a second internal end 24*b* without intersecting the external edge 20*a* or the internal edge 20*b* or the side edges 20*c* of the respective element 20 of the third set. Likewise, each slot 25 of each element 22 of the fourth set extends from a first internal end 25*a* to a second internal end 25*b* without intersecting the external edge 22*a* or the internal edge 22*b* or the side edges 22*c* of the respective element 22 of the fourth set.

It should be noted that also the internal edge 22*b* of the elements 22 of the fourth set is curved and has the same curvature as the elements 13*b* of the second set inasmuch as it is also suitable for contacting the external surface of the forming drum and defining part of the curved inner surface of the supporting structure 10.

According to an alternative embodiment of the supporting structure that is not shown in the figures, the cuts 14 of each element 12 of the first set extend from the external edge 12*a* to the internal edge 12*b* without intersecting the internal edge 12*b* and the cuts 15 of each element 13 of the second set extend from the internal edge 13*b* to the external edge 13*a* without intersecting the external edge 13*a*.

In this manner, each element 13 of the second set can be wedged above a plurality of elements 12 of the first set. What has been said previously with regard to the internal edge 12*b* of the elements 12 of the first set and to the internal edge 13*b* of the elements 13 of the second set remains valid, i.e. the internal edge 12*b* and/or the internal edge 13*b* can be curved if they are intended to define the curved inner surface of the supporting structure 10 intended to contact, and to be fixed to, the forming drum.

In a method for making a forming pocket (which is not illustrated), the forming pocket is suitable for receiving particulate material and forming conglomerates from the particulate material to be used as absorbent padding for hygienic products, wherein the forming pocket comprises: an external forming substrate (which is not illustrated) suitable for receiving the particulate material, which is provided with openings and has a shape conjugated to the form of the absorbent padding to be made; a grid supporting structure 10 provided with openings, which is coupled with the external substrate to support the external substrate during sucking of the particulate material through the external substrate and has an external surface intended for contact with the external substrate and is of a shape conjugated to the shape of the external substrate.

The method comprises obtaining from at least one first metal sheet 26 a first set of elements 12 and a second set of elements 13 made of sheet metal, each of which has a plurality of comb-shaped cuts, identified respectively by 14 and 15.

In order to obtain the aforesaid elements 12 of the first set and/or the elements 13 of the second set and/or the comb-shaped cuts 14 and 15, the method provides photochemical etching of the first metal sheet to obtain etched contours 12' and 13', 14' and 15' that define the perimeter of the elements 12 of the first set and the perimeter of the elements 13 of the second set and further define the respective cuts 14 and 15.

After separating the elements 12 of the first set and the elements 13 of the second set from the first metal sheet 26 along the respective etched contours 12' and 13', it is thus possible to wedge the elements 12 of the first set with the elements 13 of the second set by the respective cuts 14 and 15 for making the grid supporting structure 10.

With regard to what was said previously, the elements 12 of the first set are wedged on a plurality of elements 13 of the second set, sliding the cuts 14 of the internal edge 12*b* of the elements 12 of the first set on the cuts 15 of the external edge 13*a* of the elements 13 of the second set (FIG. 7).

Optionally, the method can comprise welding the elements 12 of the first set to the elements 13 of the second set at intersections between the elements, to stabilise further the grid supporting structure 10 and eliminate possible sliding between the elements 12 and 13.

The method further comprises obtaining from the first metal sheet 26 and/or from a second metal sheet (which is not illustrated), a third set of elements 20 made of sheet metal and a fourth set of elements 22 made of sheet metal, in particular performing photochemical etching, obtaining etched contours (not shown) that define the perimeter of the elements 20 of the first set and the perimeter of the elements 22 of the second set.

After separating the elements 20 of the third set and the elements 22 of the fourth set from the metal sheet 26 along the respective etched contours, the elements 20 of the third set are wedged with the elements 22 of the fourth set, in particular by coupling the protrusions 20*d* with the respective recesses 22*d*, for making a stabilising frame 19 of the grid supporting structure. Two opposite frontal walls 21 are then provided that are obtained from the elements 20 of the third set and two opposite side walls 23 obtained from the elements 22 of the fourth set.

Figure 10:
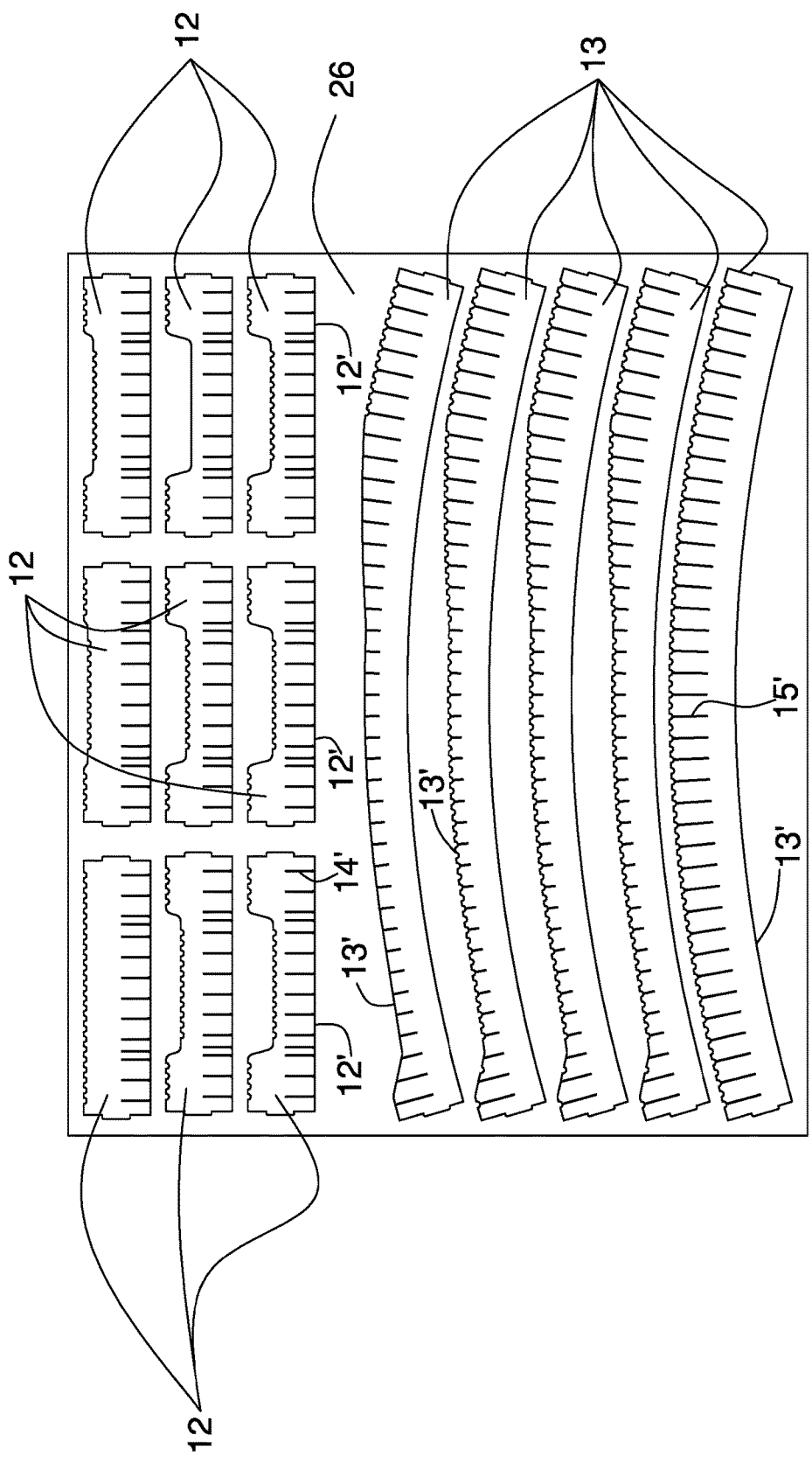
FIG. 10 is a view of a metal sheet in which cut contours are obtained of a first set of elements and of a second set, in a preliminary step of making the supporting structure in which the elements of the first and of the second set are still associated with the metal sheet.

It is noted that the elements 12 of the first set, the elements 13 of the second set, the elements 20 of the third set and the elements 22 of the fourth set can all be obtained from a single metal sheet, like the sheet 26 of FIG. 10, or from two or more metal sheets, according to constructional needs.

Photochemical etching of the metal sheet/s is based on constructional drawings of each element to be made.

The method according to the present invention completes the supporting structure 10 of the forming pocket by wedging the protruding ends 13*d* of side edges 13*c* of elements 13 of the second set in slots of elements 20 of the third set and further wedging protruding ends 12*d* of side edges 12*c* of elements 12 of the first set in slots of elements 22 of the fourth set to stabilise the grid supporting structure 10 obtained by the elements 12 and 13 with the frame 22.

Optionally, the method can comprise welding the elements 12 of the first set and the elements 13 of the second set respectively to the front walls 21 and to the side walls 23 of the stabilising frame 19, at the wedge in the respective slots 24 and 25, to stabilise further the grid supporting structure obtained by the elements 12 and 13 with the frame 22.

Owing to the invention, it is possible to obtain a method for making the supporting structure 10 of the forming pocket that does not require dedicated equipment but for which it is sufficient to provide constructional drawings of each element that is part of the supporting structure and perform via these constructional drawings a process of photochemical etching of a metal sheet for making the elements 12 of the first set, the elements 13 of the second set and optionally the elements 20 of the third set and the elements 22 of the fourth set.

Starting with these elements, assembly instructions are sufficient with the positioning detail of each element to enable any mechanical workshop to assemble the supporting structure in a simple manner.

It should be noted that the shape of the external surface of the grid supporting structure 10 is defined by the set of the external edges of the elements 12 of the first set and of the external edges of the elements 13 of the second set (and also optionally by the external edges of the elements 20 of the third set and of the elements 22 of the fourth set) and thus any hollow zone of the external surface is easily makeable by suitable positioning of shaped elements 12 or 13, in which each element has a specific shape for the hollow zone to be obtained.

In other words, assembly, and possibly welding, of the various elements already defines in itself any hollow zone of the supporting structure and no further processing of the formed grid is necessary, for example it is not necessary to perform prior art chemical etching.

Likewise, the same considerations apply to the inner surface of the supporting structure, caused by the set of the internal edges of the elements 12 of the first set and/or of the internal edges of the elements 13 of the second set, the curvature of which is easily achievable by suitable positioning of shaped elements 12 or 13, in which each element 12 or 13 is shaped with the specific shape for the curvature to be obtained.

As a result, the method for making the grid supporting structure 10 of the present invention involves only a few constructional steps, does not require dedicated equipment and further enables passing from a first supporting structure shaped in a first manner to a second supporting structure shaped in a second manner by only modifying the constructional drawings and positioning the elements 12 of the first set and the elements 13 of the second set, without the need to have different production machinery or additional processing steps.

The grid supporting structure 10 resulting from this method is simple and cheap to make.

Owing further to making the grid supporting structure by elements 12 of the first set and elements 13 of the second set wedged together by respective cuts 14 and 15, it is possible to choose the thickness of the first elements 12 and/or the thickness of the second elements 13 and/or the positioning of the respective cuts 14 and/or 15 to modify the dimensions of the sucking cells defined between the elements 12 and 13.

For example, a supporting structure can have differentiated sucking areas just by modifying the positioning of some elements 12 or 13 to make the conglomerate more compact that is obtainable from sucking the particulate material.

The invention claimed is:

1. A method of making a forming pocket suitable for receiving particulate material and forming conglomerates from said particulate material to be used as an absorbent padding for hygienic products, wherein the forming pocket comprises:
    an external forming substrate configured to receive the particulate material, the external substrate having openings and having a shape conjugated to a form of the absorbent padding to be made;
    a grid supporting structure having openings, the grid supporting structure being coupleable with the external substrate to support said external substrate during suction of the particulate material through the external substrate and having an external surface configured for contact with the external substrate, the external surface having a shape conjugated to the shape of the external substrate;
    wherein the method comprises:
    obtaining from at least one first metal sheet a first set of elements and a second set of elements made of sheet metal, each of the elements of the first and second sets having a plurality of comb-shaped cuts; and
    wedging the elements of the first set with the elements of the second set by said cuts to make a grid of said grid supporting structure;
    obtaining from the first metal sheet and/or from a second metal sheet a third set of elements made of sheet metal and a fourth set of elements made of sheet metal;
    wedging the third set of elements with the fourth set of elements to make a stabilisation frame of the grid, wherein the stabilisation frame comprises two opposite front walls obtained from said elements of the third set and two opposite side walls obtained from said elements of the fourth set, wherein each element of the third set and each element of the fourth set has a respective external edge configured for defining part of the external surface of the grid supporting structure, a respective internal edge opposite said respective external edge, and side edges;
    wherein the side edges of each element of the third set are wedged with side edges of two elements of the fourth set, and the side edges of each element of the fourth set are wedged with side edges of two elements of the third set; and
    wedging protruding ends of side edges of the elements of the second set in slots of the elements of the third set, and further wedging protruding ends of side edges of the elements of the first set in slots of the elements of the fourth set to stabilise said supporting grid structure with said frame.

2. The method according to claim 1, wherein said obtaining said elements of the first set and/or said elements of the second set comprises performing photochemical etching on the first metal sheet.

3. A forming pocket, suitable for receiving particulate material and forming conglomerates from said particulate material to be used as an absorbent padding for hygienic products, the forming pocket comprising:
    an external forming substrate configured to receive the particulate material, the external substrate having openings and having a shape conjugated to a shape of the absorbent padding to be made;

a grid supporting structure having openings, the grid supporting structure being coupleable with the external substrate to support said external substrate during suction of the particulate material through the external substrate and having an external surface configured for contact with the external substrate, the external surface having a shape conjugated to the shape of the external substrate;

wherein the grid supporting structure comprises a first set of elements and a second set of elements made of sheet metal, each of the elements of the first and second sets having a plurality of comb-shaped cuts, wherein the elements of the first set are configured for wedging in the elements of the second set via said cuts to make a grid of said grid supporting structure;

wherein the grid supporting structure comprises a stabilisation frame having a third set of elements made of sheet metal that are configured for making two opposite front walls of the frame and a fourth set of elements made of sheet metal that are configured for making two opposite side walls of the frame;

wherein the elements of the third set are configured to wedge the elements of the fourth set for making the frame;

wherein each element of the third set and each element of the fourth set has a respective external edge configured for defining part of the external surface of the grid supporting structure, a respective internal edge opposite said respective external edge, and side edges;

wherein the side edges of each element of the third set are wedged with side edges of two elements of the fourth set, and the side edges of each element of the fourth set are wedged with side edges of two elements of the third set, wherein each element of the third set has a plurality of slots that are configured to receive protruding ends of side edges of the elements of the second set; and wherein each element of the fourth set has a plurality of slots that are configured to receive corresponding protruding ends of side edges of the elements of the first set.

4. The forming pocket according to claim 3, wherein each element of the first set and each element of the second set has a respective external edge configured to define part of the external surface of the grid supporting structure, a respective internal edge opposite said respective external edge, and side edges.

5. The forming pocket according to claim 4, wherein the cuts of each element of the first set extend from the internal edge to the external edge without intersecting the external edge and/or wherein the cuts of each element of the second set extend from the external edge to the internal edge without intersecting the internal edge.

6. The forming pocket according to claim 3, wherein each slot of each element of the third set extends from a first end to a second end without intersecting the external edge, the internal edge or the side edges of the respective element of the third set; and wherein each slot of each element of the fourth set extends from a first end to a second end without intersecting the external edge, the internal edge or the side edges of the respective element of the fourth set.

7. A forming apparatus for making an absorbent padding for hygienic products, comprising:

a forming conveyor of the absorbent padding comprising at least one forming pocket, said forming pocket having:

an external forming substrate configured to receive the particulate material, the external substrate having openings and having a shape conjugated to a shape of the absorbent padding to be made;

a grid supporting structure having openings, the grid supporting structure being coupleable with the external substrate to support said external substrate during suction of the particulate material through the external substrate and having an external surface configured for contact with the external substrate, the external surface having a shape conjugated to the shape of the external substrate;

wherein the grid supporting structure comprises a first set of elements and a second set of elements made of sheet metal, each of the elements of the first and second sets having a plurality of comb-shaped cuts, wherein the elements of the first set are configured for wedging in the elements of the second set via said cuts to make a grid of said grid supporting structure;

wherein the grid supporting structure comprises a stabilisation frame having a third set of elements made of sheet metal that are configured for making two opposite front walls of the frame and a fourth set of elements made of sheet metal that are configured for making two opposite side walls of the frame;

wherein the elements of the third set are configured to wedge the elements of the fourth set for making the frame, wherein each element of the third set and each element of the fourth set has a respective external edge configured for defining part of the external surface of the grid supporting structure, a respective internal edge opposite said respective external edge and side edges;

wherein the side edges of each element of the third set are wedged with side edges of two elements of the fourth set and the side edges of each element of the fourth set are wedged with side edges of two elements of the third set, wherein each element of the third set has a plurality of slots that are configured to receive protruding ends of side edges of the elements of the second set; and wherein each element of the fourth set has a plurality of slots that are configured to receive corresponding protruding ends of side edges of the elements of the first set.

8. The forming apparatus according to claim 7, wherein the forming conveyor is a forming drum and the grid supporting structure comprises a curved internal surface configured for contact with the forming drum, the grid supporting structure having a shape conjugated to an external surface of the forming drum, and wherein the internal edge of each element of the second set is configured to define part of said curved internal surface of the grid supporting structure.

* * * * *